US012011572B2

(12) United States Patent
Baker et al.

(10) Patent No.: US 12,011,572 B2
(45) Date of Patent: Jun. 18, 2024

(54) RESETTABLE LATERAL ACTUATION MEMBER-ACTIVATED AUTOINJECTOR TRAINING DEVICE

(71) Applicant: NOBLE INTERNATIONAL, LLC, Orlando, FL (US)

(72) Inventors: Jeff Baker, Orlando, FL (US); Christopher Wai Yin Chung, Orlando, FL (US); Shishuang Hou, Ningbo (CN)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 700 days.

(21) Appl. No.: 17/256,418

(22) PCT Filed: Jun. 28, 2019

(86) PCT No.: PCT/US2019/039812
§ 371 (c)(1),
(2) Date: Dec. 28, 2020

(87) PCT Pub. No.: WO2020/006400
PCT Pub. Date: Jan. 2, 2020

(65) Prior Publication Data
US 2021/0268198 A1  Sep. 2, 2021

Related U.S. Application Data

(60) Provisional application No. 62/691,569, filed on Jun. 28, 2018.

(51) Int. Cl.
*G09B 23/28* (2006.01)
*A61M 5/315* (2006.01)

(52) U.S. Cl.
CPC ...... *A61M 5/31543* (2013.01); *A61M 5/3157* (2013.01); *A61M 5/31585* (2013.01); *G09B 23/285* (2013.01); *A61M 2205/581* (2013.01)

(58) Field of Classification Search
CPC ......... G09B 23/28; G09B 23/285; A61M 5/20
See application file for complete search history.

(56) References Cited

U.S. PATENT DOCUMENTS

| 5,137,516 A | * | 8/1992 | Rand | A61M 5/3202 |
| | | | | 604/137 |
| 7,682,155 B2 | * | 3/2010 | Raven | G09B 23/285 |
| | | | | 434/262 |

(Continued)

FOREIGN PATENT DOCUMENTS

| WO | 2016203058 A1 | 12/2016 |
| WO | 2017144211 A1 | 8/2017 |

(Continued)

OTHER PUBLICATIONS

PCT/US2019/039812; PCT Search Report & Written Opinion, Date Mailed Oct. 18, 2019, 8 pages.

*Primary Examiner* — Kurt Fernstrom
(74) *Attorney, Agent, or Firm* — Timothy H. Van Dyke; WOLTER, VAN DYKE, DAVIS, PLLC

(57) ABSTRACT

In embodiments herein, a resettable auto injection training device is provided, wherein actuation of the device requires both safety shield actuation and actuation member actuation. The training device includes audible feedback signaling actuation and completion of injection simulation. The training device audible feedback may be provided by movement of mechanical components relative to one another in embodiments herein. Further embodiments include safety features provided by compression of the safety shield post training to lock a plunger and injection simulation device within the training device until reset.

20 Claims, 16 Drawing Sheets

(56) References Cited

U.S. PATENT DOCUMENTS

| | | | | |
|---|---|---|---|---|
| 8,714,984 | B2* | 5/2014 | Mach | A61M 5/20 434/272 |
| 9,443,445 | B2* | 9/2016 | Laurusonis | G09B 23/285 |
| 9,805,621 | B2* | 10/2017 | Baker | G09B 23/285 |
| 9,911,364 | B2* | 3/2018 | Baker | G09B 23/285 |
| 10,013,895 | B2* | 7/2018 | Swanson | G09B 23/285 |
| 10,089,902 | B2* | 10/2018 | Baker | G09B 19/24 |
| 10,235,905 | B2* | 3/2019 | Su | G09B 23/285 |
| 10,255,827 | B2* | 4/2019 | Bendek | G09B 23/285 |
| 2016/0293058 | A1 | 10/2016 | Gaillot et al. | |
| 2017/0148354 | A1* | 5/2017 | Baker | A61M 5/326 |

FOREIGN PATENT DOCUMENTS

| | | | | |
|---|---|---|---|---|
| WO | WO-2017144211 A1 * | 8/2017 | | A61M 5/326 |
| WO | 2020006400 A1 | 1/2020 | | |

* cited by examiner

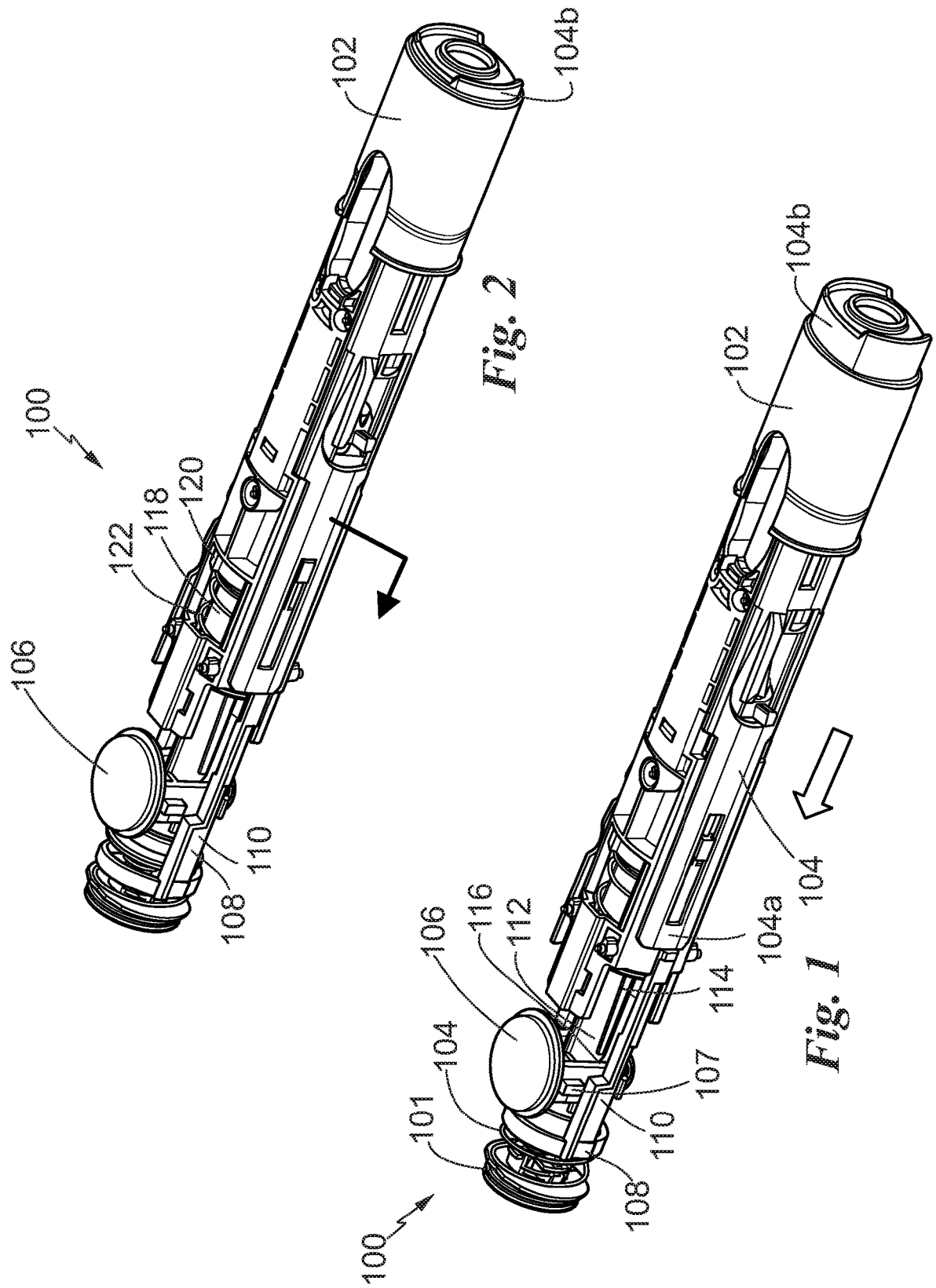

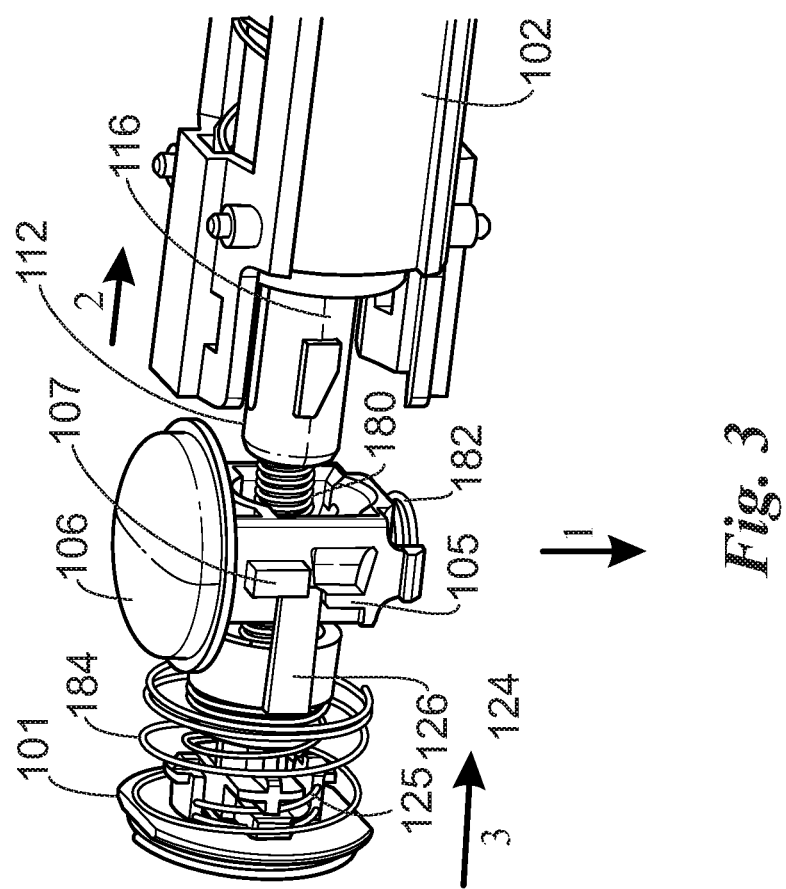

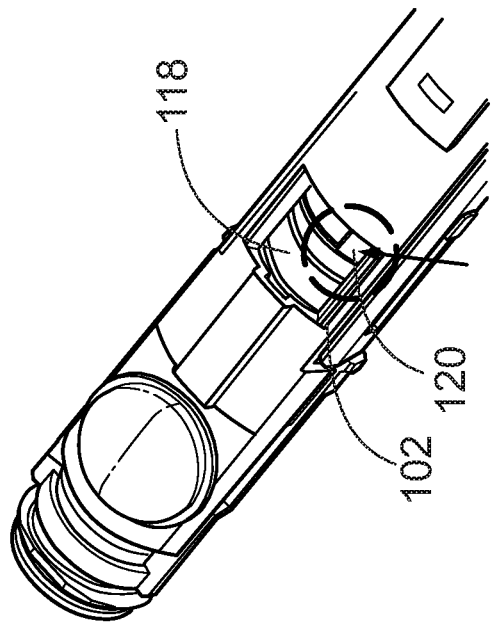
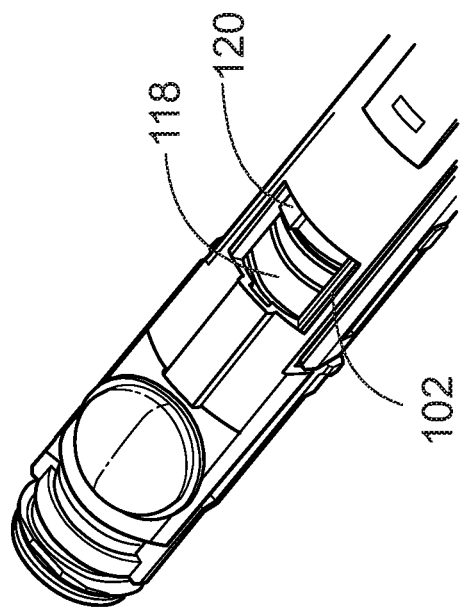

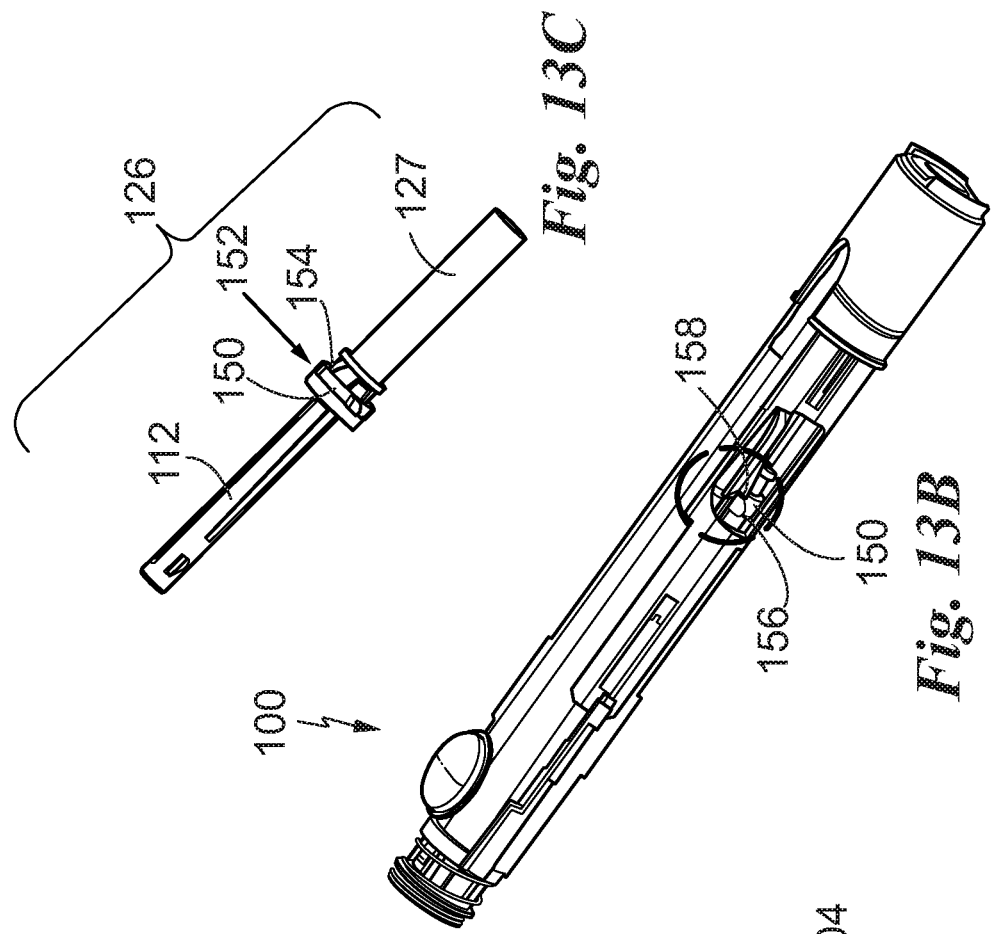
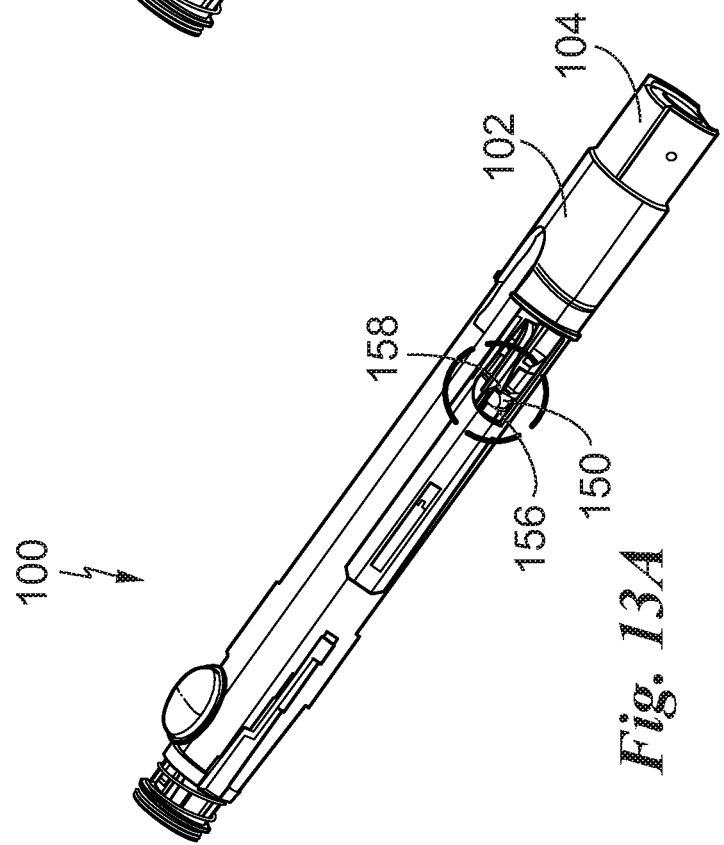

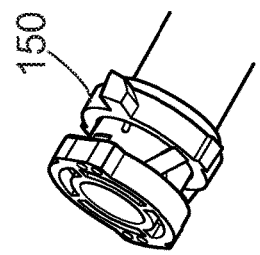
*Fig. 14E*
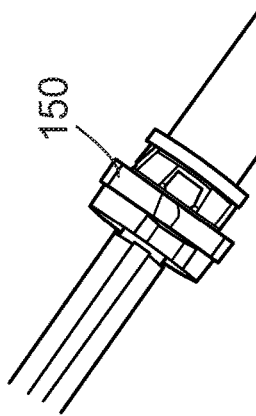
*Fig. 14B*
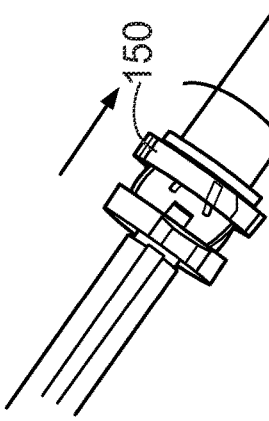
*Fig. 14D*
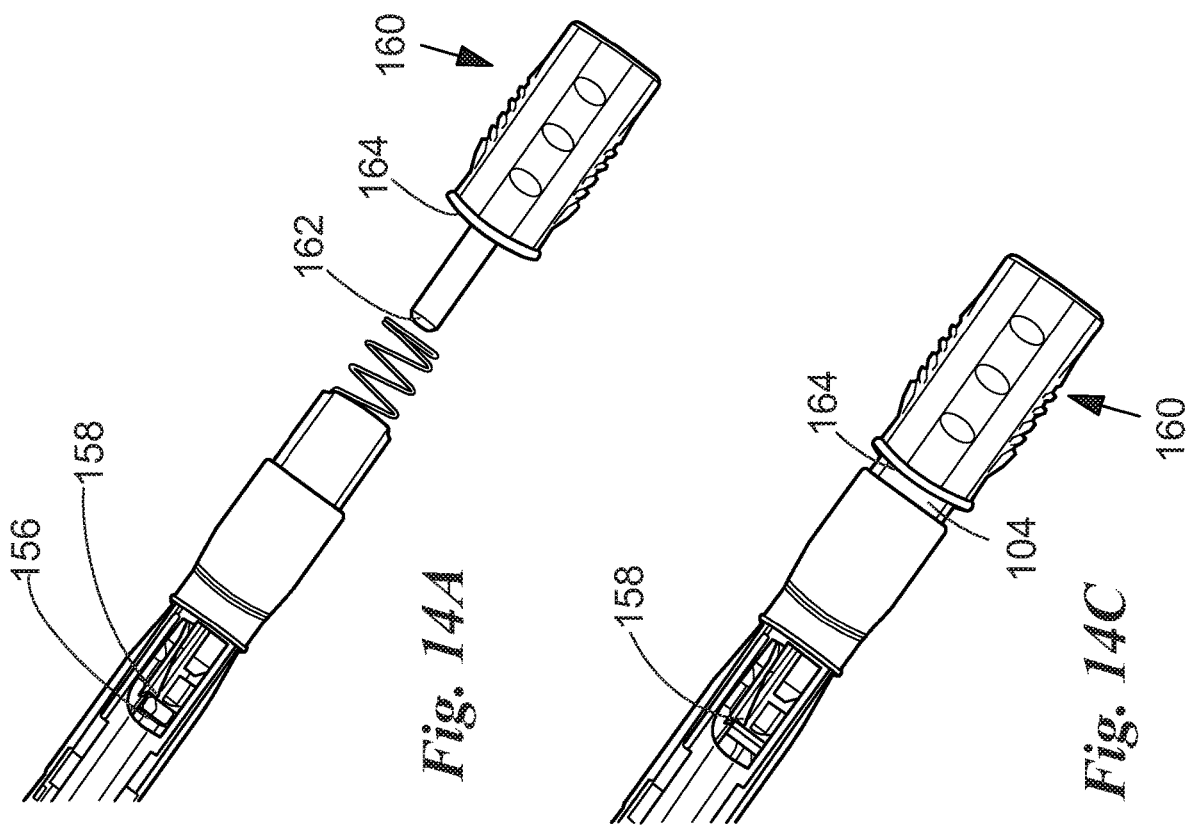
*Fig. 14A*
*Fig. 14C*

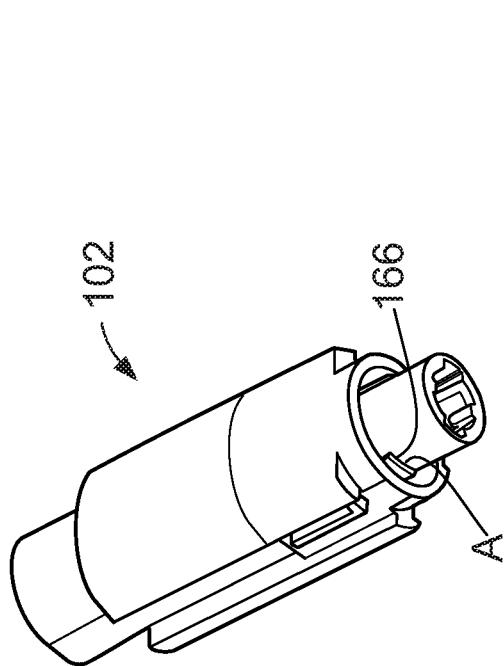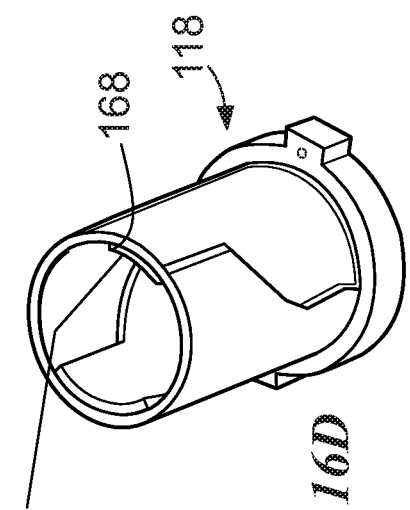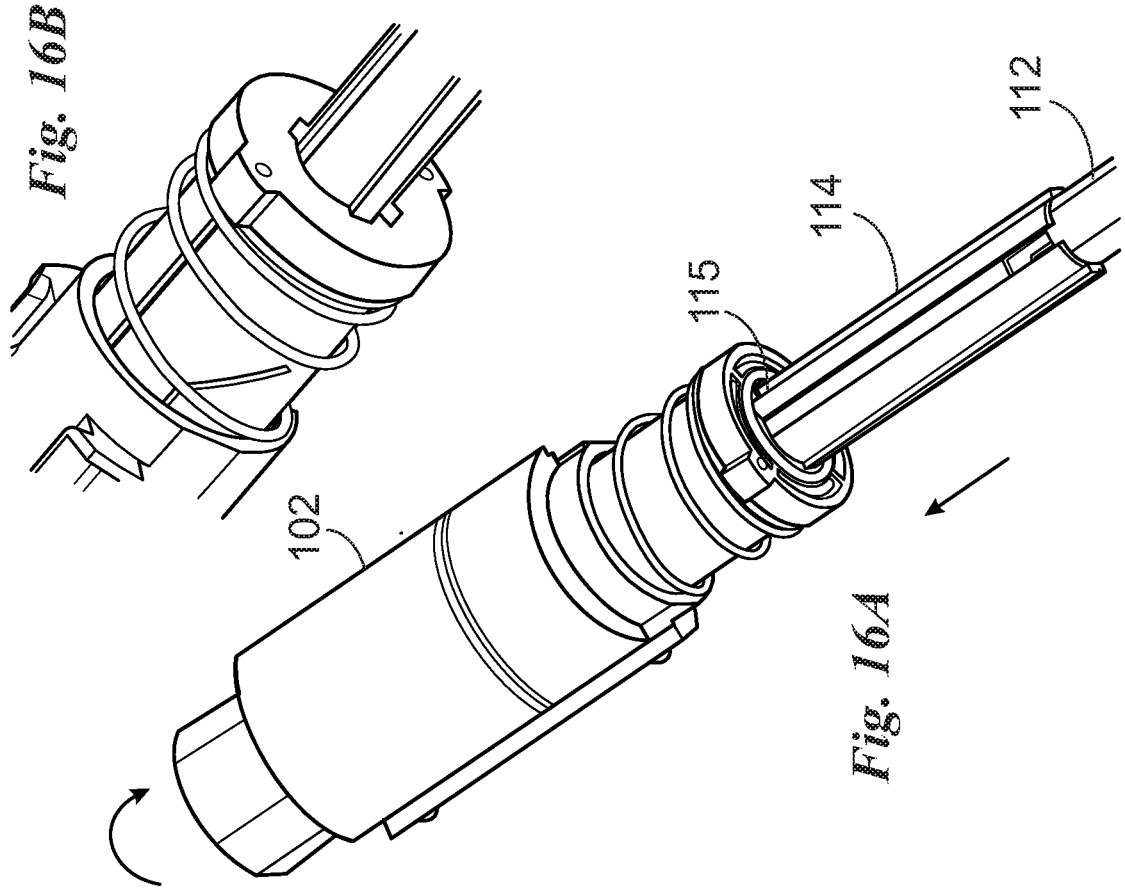

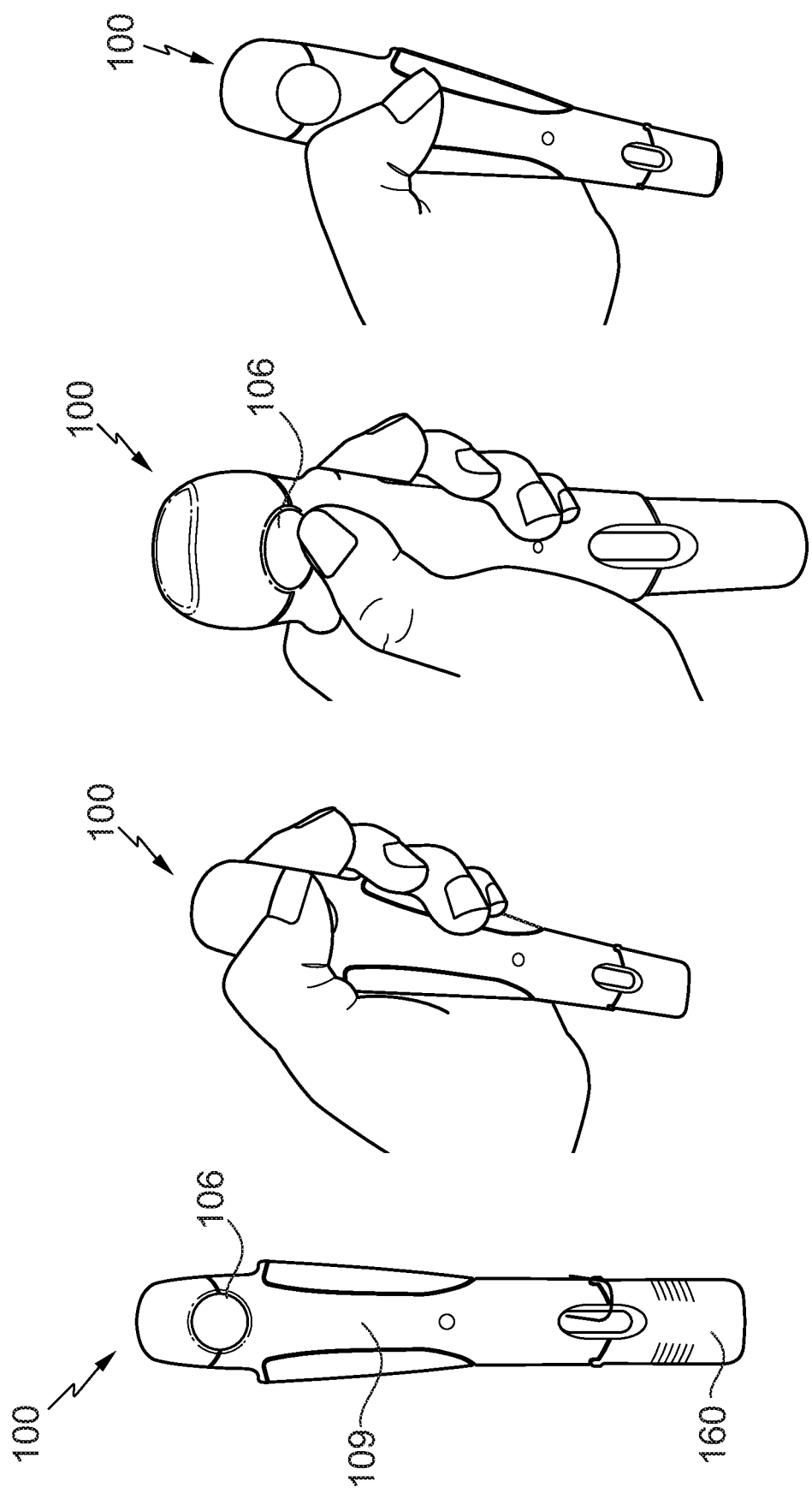

RESETTABLE LATERAL ACTUATION MEMBER-ACTIVATED AUTOINJECTOR TRAINING DEVICE

CROSS REFERENCE TO RELATED APPLICATIONS

This application claims priority to U.S. Provisional Application No. 62/691,562, filed Jun. 28, 2018, in accordance with 35 USC 119. The entirety of each of this application is incorporated by reference herein.

BACKGROUND

Injection devices have recently become increasingly popular for single dose or multi-dose, at home self-administration. These devices include both auto-injection devices and pre-filled syringe devices and are often designed to accomplish two basic objectives: convenience of drug delivery in an outpatient or at home setting, and/or automation of drug delivery in an outpatient or at-home setting.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

An additional concern exists with regard to injection devices is that users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery. Safe use and re-use of these training devices requires a resettable device. Therefore, a device which allows repeated practice and ease of use to enhance familiarity with the injection device and the self-injection process, along with the ability to safely and efficiently reset the device is paramount to an effective device for injection training.

SUMMARY

In an embodiment, a resettable injection training device is provided, including an outer housing having a proximal end and a distal end, an inner housing including a proximal end and a distal end, and a safety shield moveable relative to the inner housing. The safety shield includes a proximal end, a distal end, and an extended pre-use position, an extended post-use position, and a retracted position. The device further includes a lateral actuation member comprising a raised position and a depressed position, a plunger having a proximal end and a distal end, the plunger moveable proximally and distally within the inner housing to simulate delivery of medicament; a plunger subassembly comprising the plunger, a first signal output audibly signaling actuation of the plunger; a second signal output audibly signaling completion of an injection simulation; and a reset cap comprising a plunger interfacing portion and a safety shield interfacing portion for resetting the safety shield and the plunger.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 1 is a perspective view of an embodiment of a resettable injection training device.

FIG. 2 is a perspective view of the embodiment of a resettable injection training device shown in FIG. 1.

FIG. 3 is a partial sectional view of a proximal end of the training device embodiment of FIG. 1.

FIGS. 10A-10B are partial sectional views of a proximal end of the training device shown in FIG. 1.

FIGS. 13A-13B are perspective views of an embodiment of a training device.

FIG. 13C is a perspective view of an embodiment of a plunger sub-assembly of the device shown in FIGS. 13A-13B.

FIG. 14A is a partial view of a distal end of an injection training device and a reset cap.

FIG. 14B is a partial view of internal components of the training device of FIG. 14A, showing the plunger sub-assembly.

FIG. 14C is a partial view of a distal end of an injection training device and a reset cap showing the reset cap inserted into the device.

FIGS. 14C-14D show side and perspective views, respectively, of the plunger sub-assembly shown in FIG. 14B.

FIG. 14E shows a perspective view of the plunger sub-assembly shown in FIG. 14D.

FIG. 16A is a partial perspective view of a proximal portion of an internal components of a training device embodiment.

FIG. 16B is a partial perspective view of a proximal portion of internal components of a training device embodiment.

FIG. 16C is a perspective view of an embodiment of an inner housing.

FIG. 16D is a perspective view of an embodiment of a rotatable member.

FIGS. 18A-18G provide a sequence of steps for using an embodiment of a training device, according to one embodiment.

DETAILED DESCRIPTION

Figure 5:
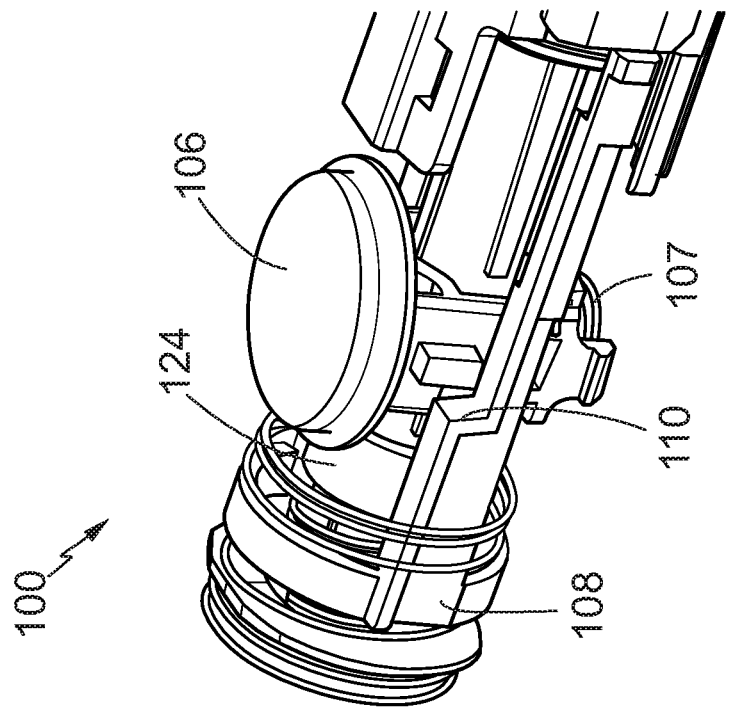
FIG. 5 is a partial sectional view of a proximal end of the training device embodiment of FIG. 1.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

The term "adjacent" as used herein, includes but is not limited to near, associated with, or in close proximity to.

In embodiments herein, an actuation member is described as being in a depressed locked position and in a released locked position. The actuation member is also described herein as being in an unlocked position, which may include a released unlocked position. In the unlocked position, the actuation member may be compressed to actuate the device. Therefore, when the actuation member is in the unlocked position, activation of the actuation member may actuate the device. The actuation member is in the unlocked position, in one embodiment, following depression (proximal movement) of the safety shield.

In embodiments herein, the safety shield is described as being in an extended, pre-use position and an extended, post-use position, an extended pre-use position refers to a position of the safety shield, extended from the distal end of the outer housing, prior to actuation of the lateral actuation member during a simulation. The safety shield in an extended, post-use position refers to a position of the safety shield, extended from the distal end of the housing, following actuation of the lateral actuation member.

In embodiments herein, the plunger is described as being in a pre-use position and a post-use position. The pre-use position of the plunger refers to its proximal position relative to the outer housing, prior to release of the plunger which occurs upon actuation of the lateral actuation member. The post-use position of the plunger refers to a distal position of the plunger relative to the housing, which occurs upon completion of the medicament delivery simulation when the plunger has reached its most distal position in the device.

In some embodiments herein, the device is described as having a pre-use position or pre-use state and a post-use position or post-use state. The pre-use position or pre-use state includes wherein the device is ready to be actuated to initiate an injection simulation, for example, before use of the device for a training, or following reset of the device. The post-use position, or post-use state includes the state of the device and its components following a simulated injection delivery, and prior to reset of the device.

The inventors herein have identified a need for a device to be used in effectively training patients to use a needle-containing injection device, particularly when these injection devices are used for at home or outpatient environments. In the field of medicament injection training devices, correct injection of medicament by way of the injection device is crucial for obtaining accurate doses of medicament contained therein. Factors such as a fear of needles, fear of pain associated with an injection, inexperience with injection devices and delivering injections, and unfamiliarity with injection devices and their operation, among other factors can contribute to issues in administering the medicament correctly with the injection device. Consequently, patient training in correct operation of the injection device is crucial to reducing patient anxiety and enhancing patient compliance. In one embodiment, a resettable injection training device is provided herein.

Turning to the Figures, FIG. 1 is a perspective view of an embodiment 100 of a resettable injection training device providing a view of the inner housing 102 and the safety shield 104 which is moveable proximally and distally relative to the inner housing 102. An outer housing of the device has been removed in the Figures shown so as to provide a complete view of the innerworkings of the device 100. The inner housing 102 having a proximal end and a distal end, and the safety shield 104 having a proximal end 104a and a distal end 104b. A lateral actuation member 106 having a lateral actuation member first tab 107 and an actuation member second tab 105 (shown in FIG. 3) is disposed along a surface of the device 100. The lateral actuation member 106 includes a released position and a depressed position. The lateral actuation member 106 is moved from the released position to the depressed position during actuation of the device 100. This movement of the lateral actuation member 106 follows retraction of the safety shield 104 as will be described in greater detail hereinafter.

The lateral actuation member 106 and the safety shield proximal end 104a are shown in FIG. 1 in contact with an actuation member released lock 108 having an actuation member released lock tab 110 and a proximal portion of the safety shield 104a. A force on the lateral actuation member 106 prior to retraction of the safety shield 104 causes the lateral actuation member tab 107 to interface with the actuation member released lock tab 110 to prevent depression of the lateral actuation member 106, in essence, to prevent actuation of the device 100 prior to proximal movement of the safety shield 104.

Upon proximal movement of the safety shield 104 relative to the outer housing by a force on the safety shield distal end 104b as shown in FIG. 2, the safety shield 104 interfaces with the actuation member released lock 108 to allow actuation of the lateral actuation member 106. The movement of the safety shield 104 in a proximal direction when the device is in a pre-use position causes the actuation member released lock to move in a proximal direction such that the actuation member released lock tab 110 moves away from the lateral actuation member first tab 107, to allow activation of the lateral actuation member 106 by moving the lateral actuation member 106 from a released position to a depressed position. Both proximal movement of the safety shield 104 and activation of the lateral actuation member 106 are required to initiate actuation of the device 100, and proximal movement of the safety shield 104 releases the lateral actuation member 106 such that it may be actuated to initiate actuation of the device 100.

The device 100 may further include a plunger 112 including a proximal plunger end 112a and a distal plunger end 112b (not visible in FIGS. 1-2). The plunger 112 includes one or more plunger rails 114 on its surface, and one or more plunger rail gaps 116. The device 100 may also include a rotatable member 118, a rotatable member tab 120, in some embodiments, and a rotatable biasing member 122 for rotating the rotatable member 118. The rotatable biasing member 122 may include a spring configured to cause resistance to rotate the rotatable member 118. In one non-limiting embodiment, the spring may include a torsion spring.

FIG. 3 shows a partial sectional view of a device embodiment 100, wherein arrows 1, 2, and 3 show the stepwise movement of the components of the device 100 in order to actuate the lateral actuation member 106. The first step includes (following proximal movement of the safety shield 104) movement of the lateral actuation member 106 from a raised position to a depressed position, causing release of the plunger 112 and thus movement of the plunger in a distal direction, resulting in movement of the actuation member depressed lock 124 such that the actuation member depressed lock tab 126 interfaces with the lateral actuation member second tab 105 to maintain the lateral actuation member 106 in a locked, depressed position until reset of the device 100.

Figure 4:
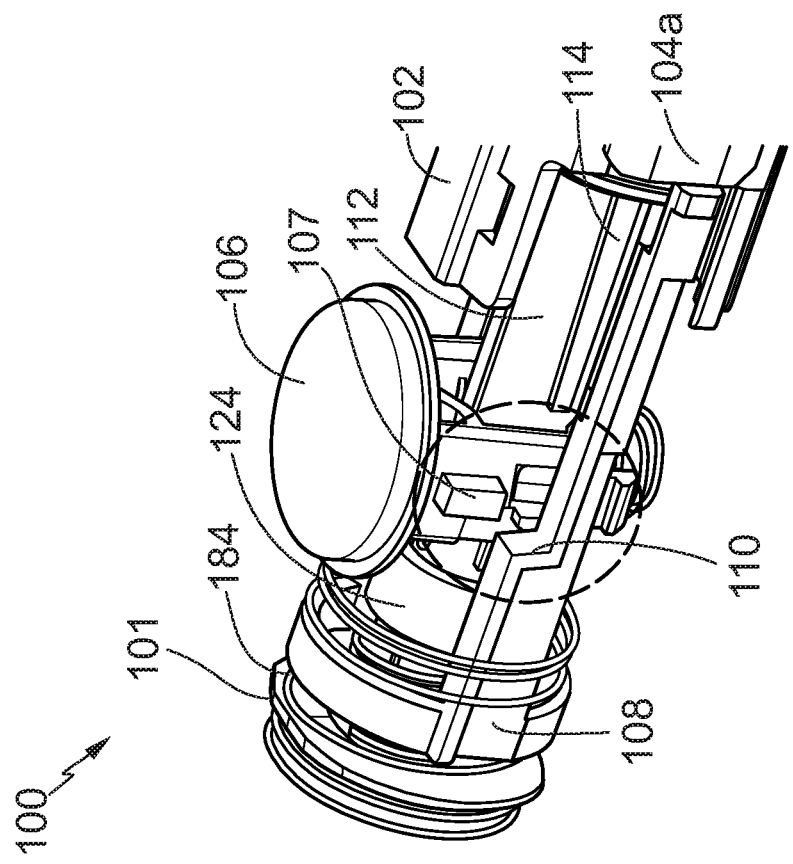
FIG. 4 is a partial sectional view of a proximal end of the training device embodiment of FIG. 1.

FIGS. 4-5 are partial sectional views of an embodiment of the device 100, showing the interactivity between the proximal end of the safety shield 104a and the actuation member released lock 108. Proximal movement of the safety shield 104 moves the actuation member released lock 108 toward the proximal end of the device 100 as shown, interrupting the contact between the actuation member released lock tab 110 and the lateral actuation member first tab 107. This "unlocking" of the lateral actuation member 106 by virtue of the interactivity described herein, as one example, allows the lateral actuation member 106 to be depressed (i.e., moved from a raised position to a depressed position) to actuate the device 100 and release the plunger 112 to simulate an injection.

Figure 6A:
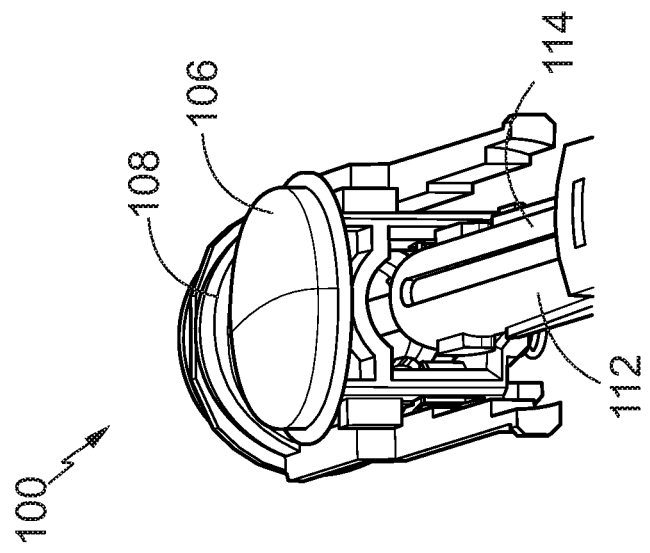
FIGS. 6A-6C are a partial sectional view of a proximal end of the training device embodiment of FIG. 1.
Figure 6B:
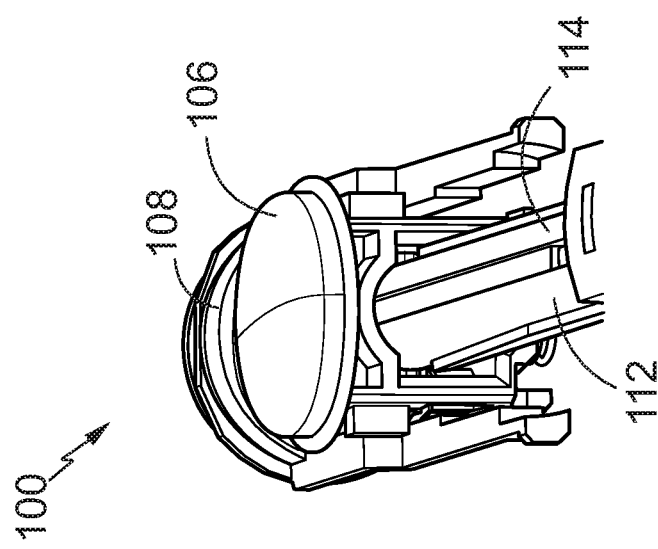
Figure 6C:
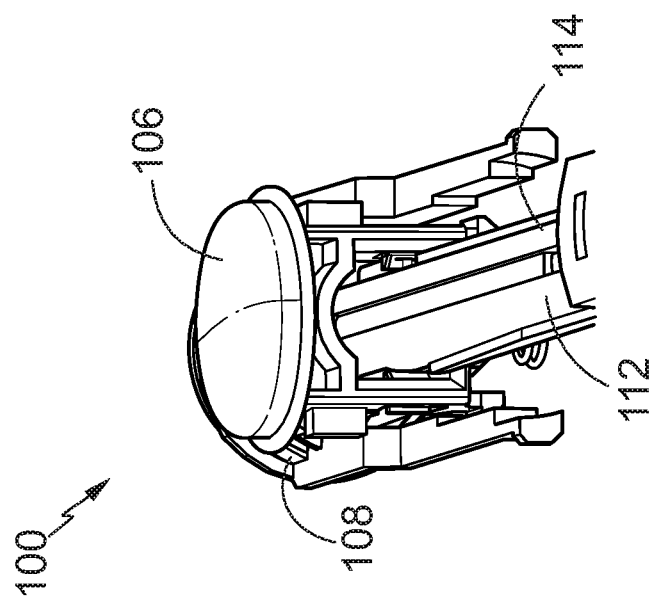
Figure 7A:
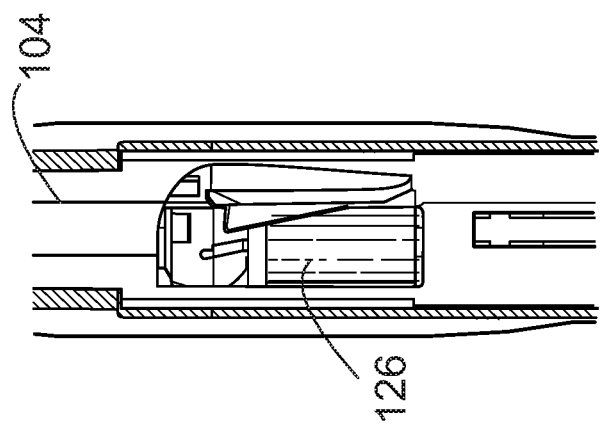
FIGS. 7A-7B are partial sectional views of a portion of the device of FIG. 1.
Figure 7B:
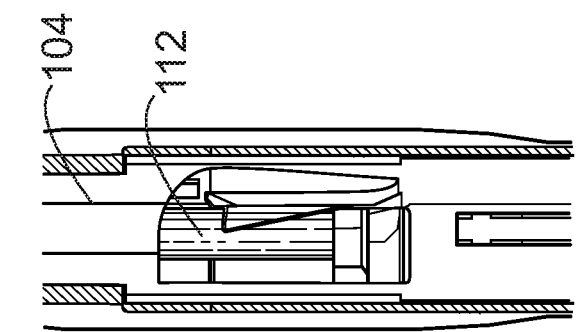
Figure 8A:
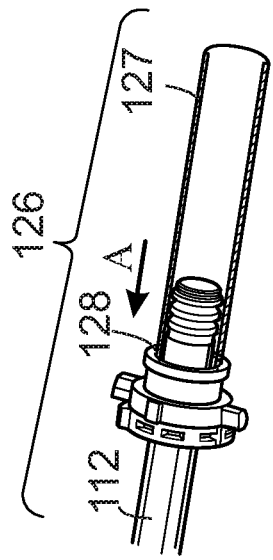
FIG. 8A is a partial sectional view of a portion of an embodiment of a plunger sub-assembly.
Figure 8B:
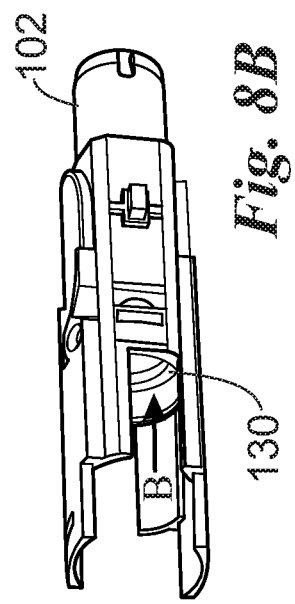
FIG. 8B is a prospective view of a portion of an internal housing of a training device embodiment.
Figure 8C:
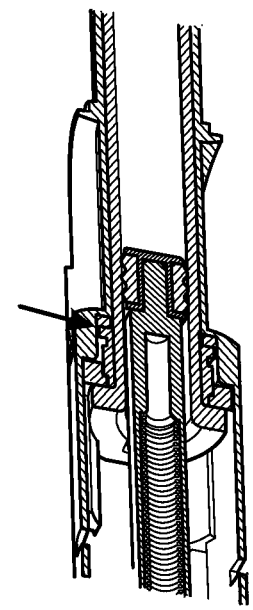
FIG. 8C is a cross sectional view of the interactivity between the plunger sub assembly shown in FIG. 8A and the internal housing shown in FIG. 8B.

Once the lateral actuation member 106 has been actuated (depressed) as shown in the stepwise movement of the actuation member 106 from released to depressed position in FIG. 6A to FIG. 6B, the plunger 112 is released as shown in FIG. 6C. Release of the plunger subassembly 126 which includes the plunger 112 and plunger receiver 127 by actuation of the lateral actuation member 106 causes the plunger subassembly 126 to move distally relative to the inner housing 102. This distal movement continues until a plunger receiver ridge 128 interfaces with an inner housing ridge 130 (inner housing ridge 130 in FIG. 8B) as shown in FIGS. 8A-8C. FIG. 7A shows a partial sectional view of the device 100, upon actuation of the lateral actuation member 106, showing the plunger subassembly 126 in a proximal position relative to the inner housing 102. After actuation of the lateral actuation member 106, the plunger subassembly 126 is released and moves distally relative to the inner housing 102 as shown in FIG. 7B. The interface between the plunger receiver ridge 128 and the inner housing ridge 130 is shown in FIG. 8C. This interface may cause a first signal output of the device 100, signaling actuation of the device 100 and delivery of the plunger subassembly 126 toward the distal end of the device to indicate actuation of a drug delivery device.

Figure 9C:
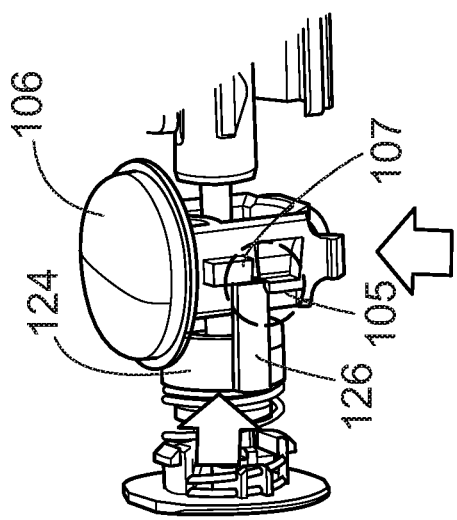
FIGS. 9A-9C are partial sectional view of a proximal end of the training device embodiment of FIG. 1 during operation.
Figure 9B:
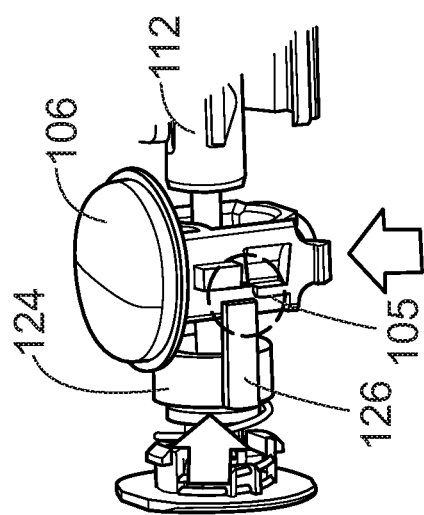
Figure 9A:
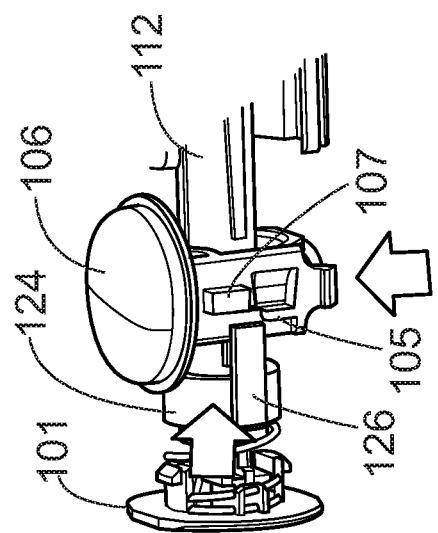

FIGS. 9A-9C provide partial sectional views of the proximal end of the device embodiment 100, showing examples of spring forces caused by the actuation member released lock spring 184, and the actuation member spring 182. The arrows shown in the FIGS. represent spring forces that are acting on the lateral actuation member toward its raised, pre-use position, and the actuation member depressed lock 124 toward a distal direction, respectively. FIG. 9A shows a partial sectional view of the proximal end of the device 100, during compression of the lateral actuation member 106 by a force on the actuation member, against the force of the actuation member spring 182. FIG. 9B shows the release of the plunger 112 following actuation of the actuation member 106, which removes the force holding the actuation member depressed lock 124 in a proximal position. Once the plunger 112 is released to move distally relative to the device 100, the actuation member depressed lock spring 125 provides a force on the actuation member depressed lock 124 as shown in the arrow superimposed over the actuation member depressed lock spring 125 in FIGS. 9A-9C, displacing the actuation member depressed lock 124 in a distal direction. FIG. 9C shows the actuation member depressed lock tab 126 interfacing with the lateral actuation member second tab 105, maintaining the lateral actuation member 106 in a depressed position following actuation.

FIGS. 10A-10B provide a partial sectional view of the proximal end of the device, during completion of the injection simulation. Once the plunger 112 has moved to its most distal position within the device 100, the rotatable member 118 rotates in a first direction. Rotation of the rotatable member 118 is controlled by or caused by a rotatable biasing member 122 force. The rotatable member 118 rotates until a rotatable member tab 120 contacts a portion of the inner housing 102 as shown in FIG. 10B, preventing further rotation of the rotatable member 118. The interaction between the inner housing 102 and the rotatable member tab 120 shown in FIG. 10B causes a second signal output. The second signal output signals to a user completion of an injection simulation, in one non-limiting embodiment.

The signal outputs described herein may include audible signal outputs in non-limiting embodiments. When the signal outputs include audible outputs, the audible output may be caused by two or more mechanical components interacting within the device. For example, interactivity between a portion of the rotatable member 118 (namely, the rotatable member tab 120) and a portion of the inner housing 102 may cause an audible sound, a signal output, signaling completion of the simulated injection. Other examples of audible signal outputs may be provided, including, but not limited to one or more speakers. The signal outputs may also, or alternatively, include visual or tactile outputs, among other types of signaling methods, for example, including LED's, transparent or translucent components of the device providing a view of the internal components and positions of each during use of the device to indicate to a user when a step in the simulation has occurred, for example movement of the rotatable member tab from a first position as shown in FIG. 10A to a second position as shown in FIG. 10B may be visible to a user as a visual output to indicate completion of a simulated injection.

Signal outputs may be configured to signal initiation or completion of various steps in use of the device. In other non-limiting embodiments, a first signal output may occur when the safety shield is moved to its proximal position within the housing, allowing actuation of the lateral actuation member 106, which may cause a second signal output signaling initiation of an injection simulation. A third signal output may occur when the plunger subassembly is delivered to the distal end of the device, wherein the plunger receiver ridge 128 and inner housing ridge 130 interface. A fourth signal output may occur when the injection simulation is completed by way of interaction between the inner housing 102 and a rotatable member tab 120 (as described in greater detail herein) causing the fourth signal output under the force of the rotatable biasing member 122, in one non-limiting embodiment. The fourth signal output may signal completion of an injection simulation. Various combinations of signal outputs, whether audible, visual, tactile or otherwise may signal steps in the use of the device to guide a user through a simulation and confirm initiation and/or completion of steps. Moreover, these signal outputs may guide a user in correct use of the device, increasing compliance.

Figure 11C:
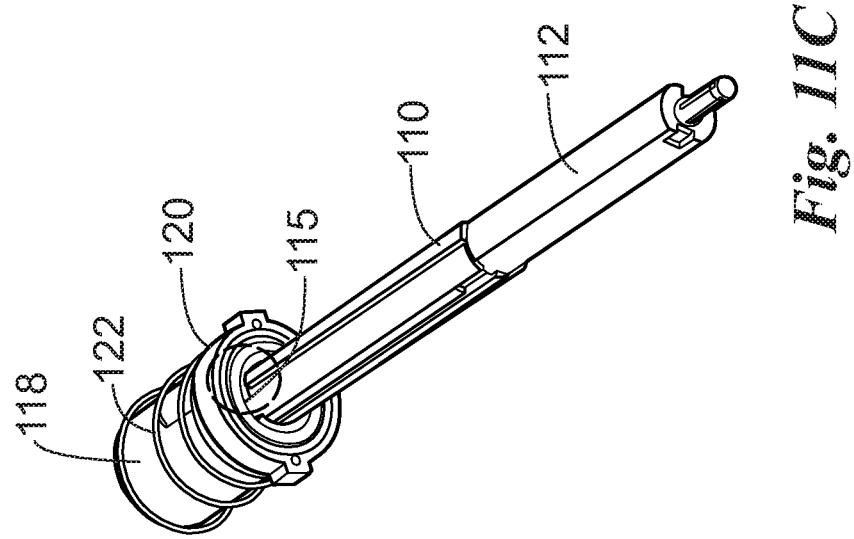
FIGS. 11A-11C are perspective views of a plunger subassembly according to one embodiment.
Figure 11B:
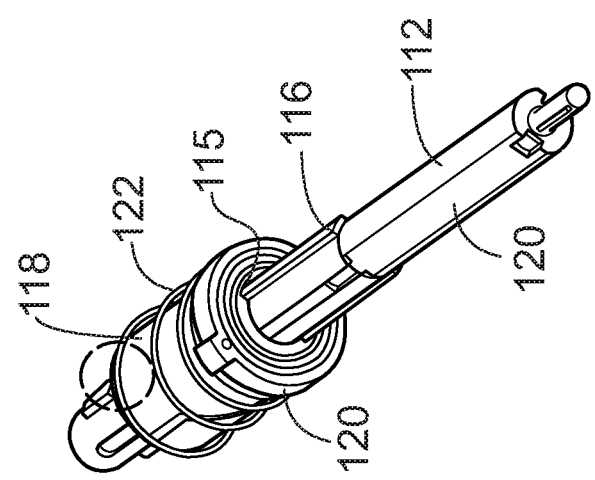
Figure 11A:
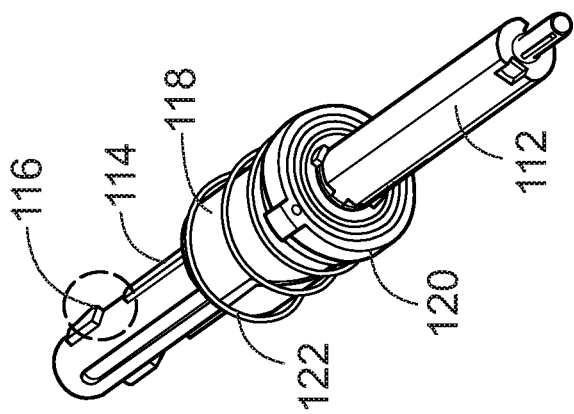

FIGS. 11A-11C include perspective view of the plunger 112 and the rotatable member 118 in order to show the interactivity between the components during use of the device, in particular, during actuation of the device. As can be seen in FIG. 11A, the at least one plunger rail 114 on the plunger 112 maintains the rotatable member in a second direction, against the force of the rotatable biasing member 122. Once the plunger 112 is released as shown in FIG. 11B it moves distally during actuation of the simulation device 100 until the plunger rails 114 pass through the rotatable member 118. Once the plunger rails 114 traverse the rotatable member 118, the rotatable member 118 is allowed to rotate. Under the force of the rotatable biasing member, the rotatable member 118 rotates in the first direction until a portion of the rotatable member (i.e., rotatable member tab 120) abuts the inner housing 102 as shown in FIG. 11C resulting in the second signal output. In one non-limiting embodiment, the second signal out pout audibly signals completion of an injection simulation.

Following simulation, the device 100 is removed from the surface of the user. As a result of removal of the force on the distal end of the safety shield 104 by removing the distal end of the device 100 from a contact surface, the safety shield 104 extends to an extended, post-use position as shown in the side sectional view of the device in FIG. 13A. FIG. 13C includes a view of the plunger subassembly with the plunger 112 showing its placement within the device 100. FIG. 13B shows a view of the device wherein the safety shield 104 has been retracted post simulation. Retraction of the safety shield 104 post simulation may occur by a force on the distal end of the safety shield 104, moving the safety shield in a proximal direction. In FIGS. 13A, 13B and 13C a ring member 150 is shown, the ring member 150 is rotatable around an inset portion 152 at the proximal end of the plunger receiver 127 of the plunger subassembly 126. The inset portion 152 includes one or more protuberances 154 for interacting with an inner surface of the ring member 150. The ring member 150 maintains axial and longitudinal movement within the inset portion 152. The ring member 150 includes one or more grooves on its inner surface which interface with the protuberances 154 of the inset portion 152. The ring member 150 also includes a projection 156 extending therefrom. The safety shield 104 includes a safety shield tab 158, wherein upon application of a force on the distal end of the safety shield 104 to move the safety shield 104 proximally, from an extended, post-use position, the safety shield tab 158 interfaces with the ring member projection 156, moving the plunger subassembly 126 proximally. This feature acts as a safety feature, so that no interaction with the plunger subassembly 126, or a possibly an injection member or injection simulation member, in some embodiments, located within a distal end of the inner portion of the device housing may be contacted by a user via the distal end of the device 100. In this manner, post use (post simulation), a force on the safety shield 104b distal end moves the safety shield 104 proximally into the device 100, but also, by the interface between the safety shield tab 158 and the ring member projection 156, this movement moves the plunger subassembly 126 proximally.

Figure 12B:
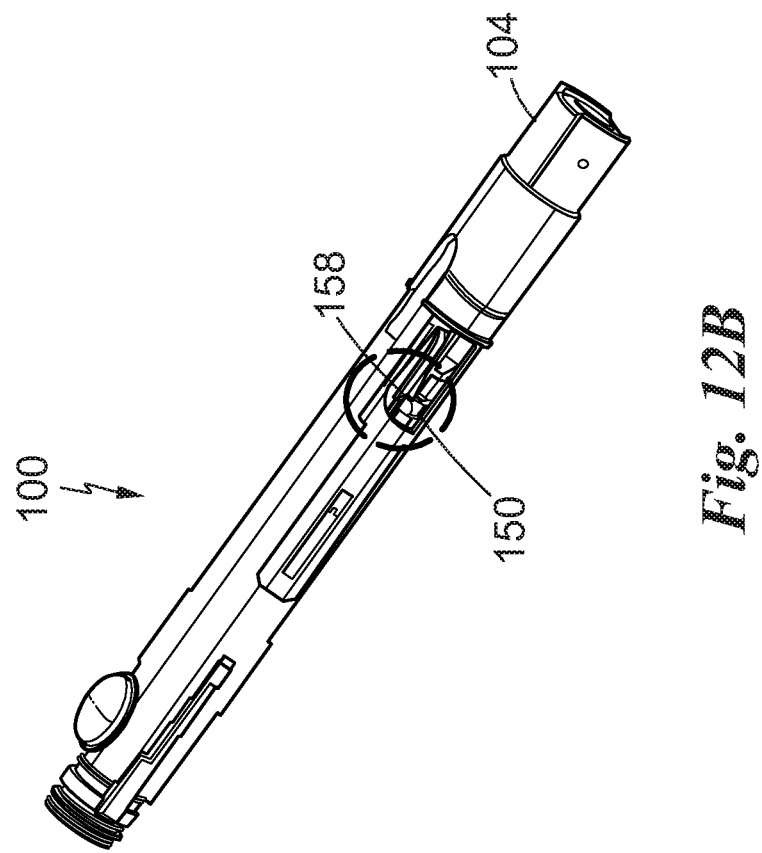
FIGS. 12A-12B are perspective views of an embodiment of a training device.
Figure 12A:
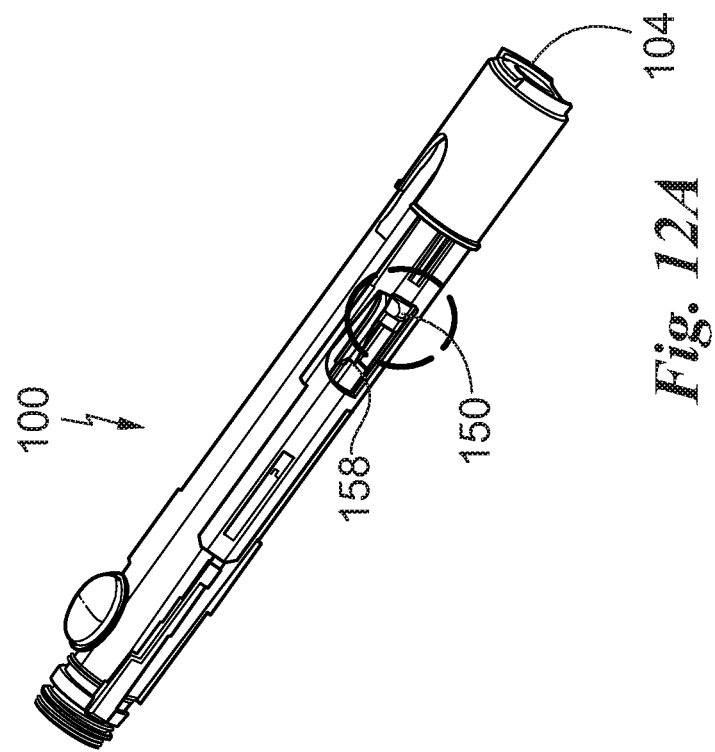

The safety shield tab 158 may be formed, in some embodiments, at least partially of a flexible material, such that it may bypass the ring member projection 156 when the safety shield 104 is extended following injection simulation (see FIGS. 12A-12B). In another embodiment, the safety shield tab 158 may include a shape such that it may bypass the ring member projection 156, when it moves in a first direction (distally) but cannot bypass the ring member projection 156 when it moves in a second direction (proximally).

In order to reset the device 100, as shown in FIG. 14A-14D, a reset cap 160, (which may act as a cap on the distal end of the device 100 to protect the device prior to use, but is removed before a simulation begins, for example), in one embodiment, is inserted into the distal end of the safety shield 104, such that a plunger interfacing portion 162 traverses an opening in the distal end of the safety shield 104 and the reset cap 160 is moved in a proximal direction relative to the device 100 until a safety shield interfacing portion 164 contacts the distal end of the safety shield 104. Continued movement of the reset cap 160 toward the device 100 causes the force on the safety shield 104 from the safety shield interfacing portion 164 to move the safety shield 104 proximally, and due to the interaction between the safety shield tab 158 and the ring member projection 156, the ring member 150 is also moved in a proximal direction relative to the plunger receiver 127. As a feature of the rotatable and moveable ring member 150 within the inset portion 152, and due to the interaction between the protuberances 154 of the inset portion, and their interaction with an inner surface of the ring member 150 as shown in FIG. 14E, the ring member 150 is rotated as it moves proximally during reset.

Figure 15B:
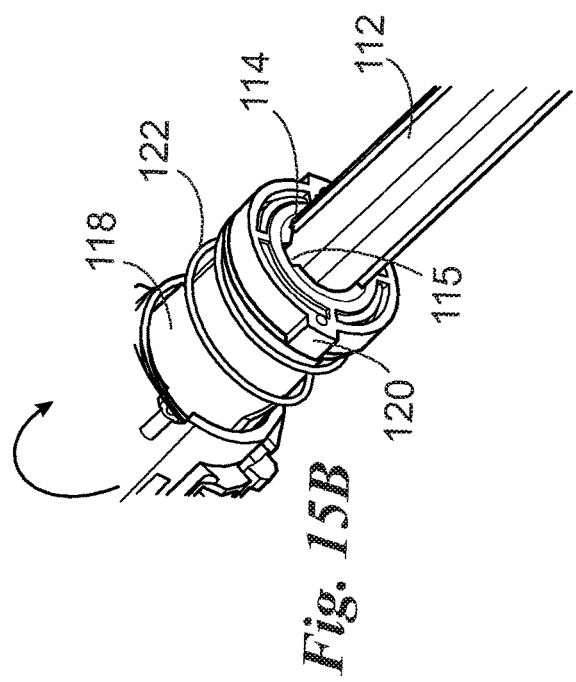
FIG. 15B is a perspective view of the portion of the training device shown in FIG. 15A.
Figure 15D:
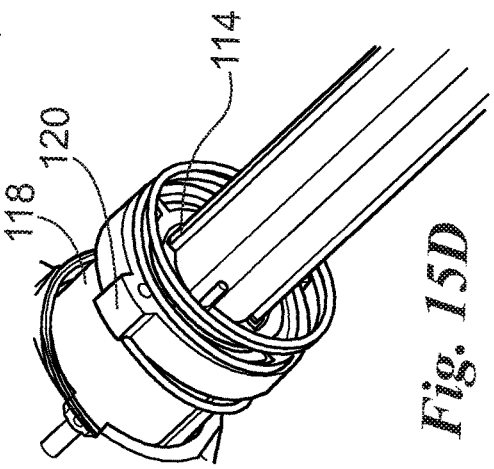
FIG. 15D is a perspective view of the portion of the training device shown in FIG. 15C.
Figure 15A:
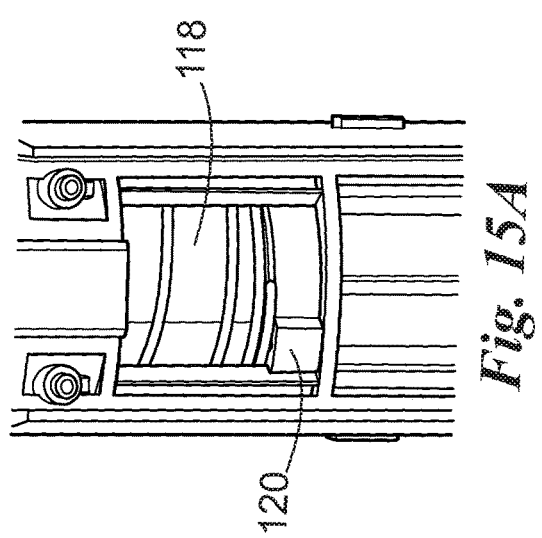
FIG. 15A is a partial side view of an embodiment of a training device.
Figure 15C:
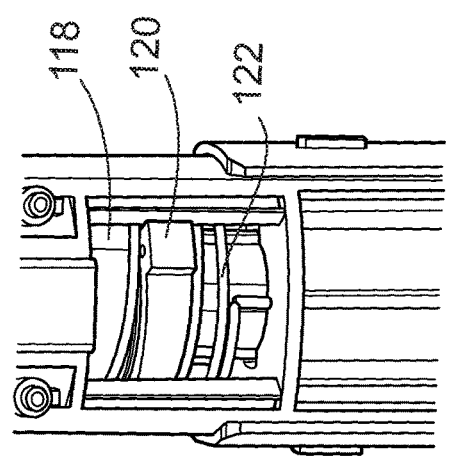
FIG. 15C is a partial side view of an embodiment of a training device.
Figure 17B:
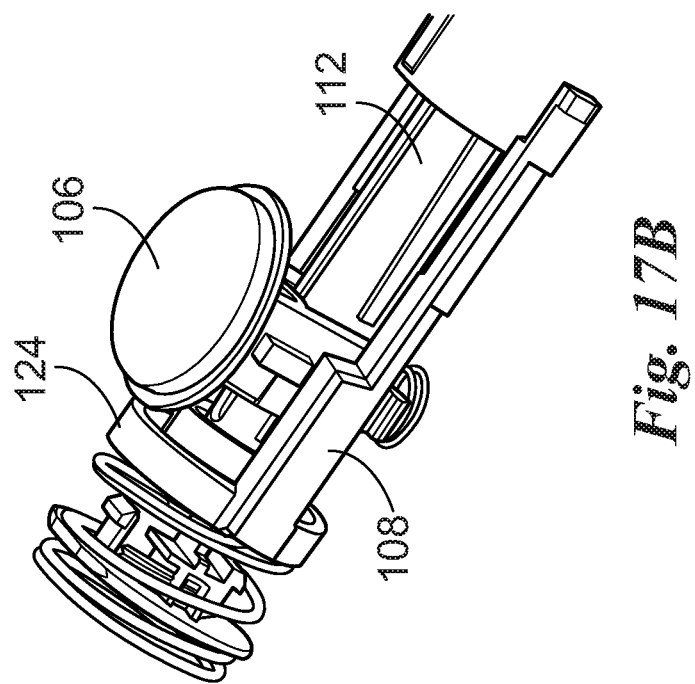
FIGS. 17A-17B are side views of internal components of a proximal end of a training device.
Figure 17A:
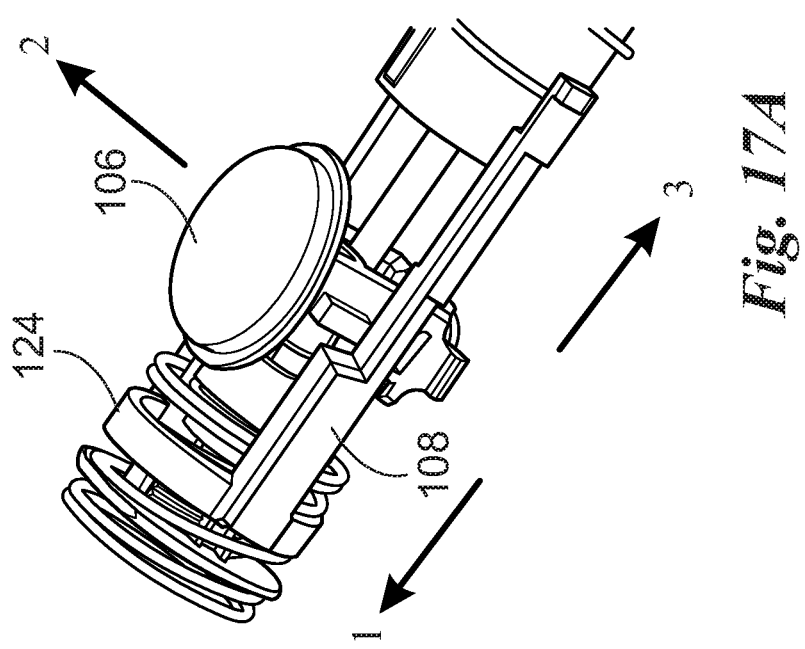

FIGS. 15A-15D provide views of a portion of the device 100 including the rotatable member 118 during reset. Movement of the plunger 112 in a proximal direction via the reset cap 160, causes the plunger rails 114 to interface with the rotatable member 118 moving the rotatable member 118 in a proximal direction as shown in FIG. 15B. The rotatable member 118 is rotated while it moves proximally by way of an interaction between one or more inner housing tabs 166 and a ramp 168 on an inner surface of the rotatable member 118 as shown in FIG. 16A-16D. Continual proximal movement of the rotatable member 118 by interface with the plunger 112 forces the ramp 168 to interface with the tabs 166 to rotate the rotatable member 118 in the second direction until the plunger rails 114 align with rotatable member notches 115 on an inner surface of the rotatable member 118, and the rotatable member tab 120 is consequently reset to a pre-use position. This operation may cause the rotatable biasing member 122 to become biased, energized, or wound, such that in a subsequent simulation, the rotatable biasing member 122 could be released causing the rotatable member to rotate. The reset cap 160 may be further moved proximally into the device 100, moving the plunger 112 proximally toward a reset position until the actuation member depressed lock 124, the actuation member released lock 108 and the lateral actuation member 106 are in the pre-use, reset position.

Figure 18G:
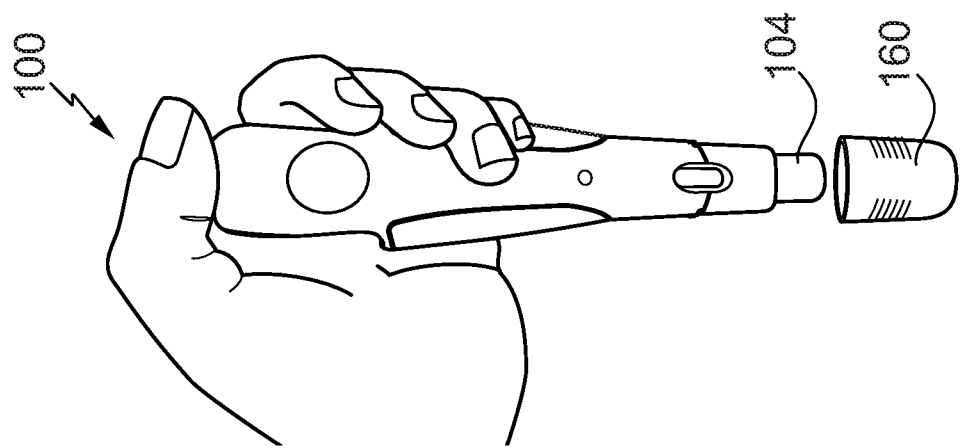
Figure 18F:
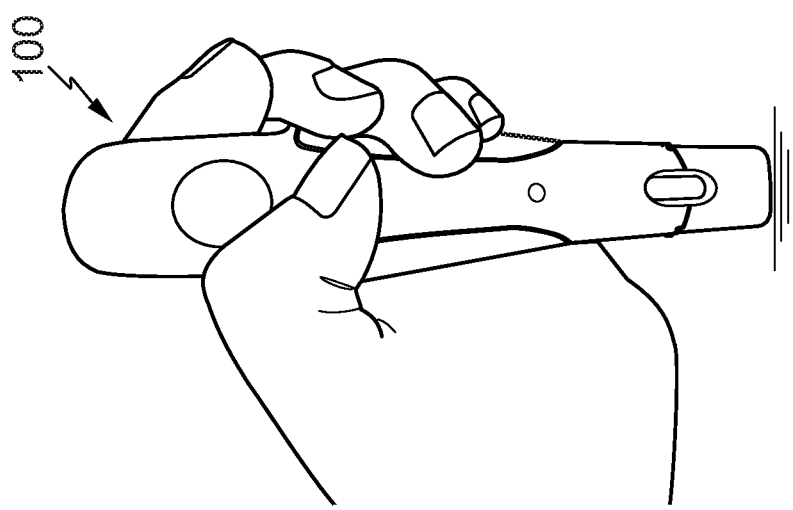
Figure 18E:
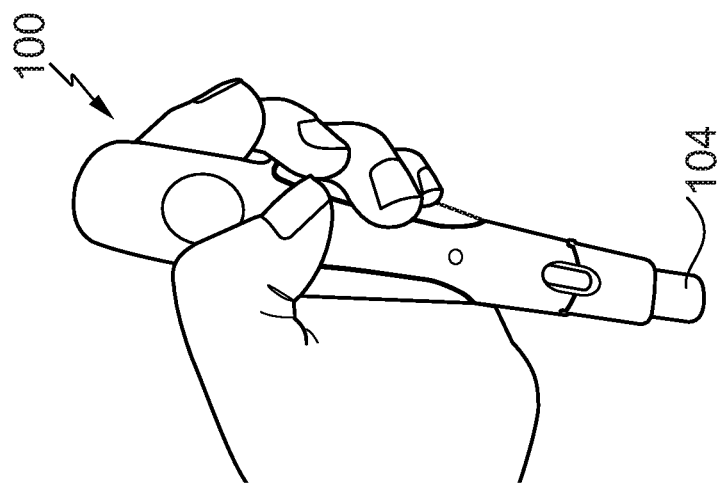

FIGS. 18A-18G include perspective views of the device embodiment 100, showing steps of use during an injection simulation and reset thereof. FIG. 18A shows the device 100 including outer housing 109, lateral actuation member 106 and reset cap 160 prior to use of the device 100. FIG. 18B shows the first steps in use of the device 100 by removing the reset cap (already removed in FIG. 18B) and depressing the safety shield 104. FIG. 18C shows the subsequent steps in use of the device 100 by pressing the lateral actuation member 106, while maintaining the safety shield 104 in a depressed state, wherein upon actuating the device 100 a first signal output is provided to indicate actuation has occurred. FIG. 18D shows continued maintenance of the safety shield 104 depressed against a contact site (i.e. the user) until a second signal output is delivered to indicate injection simulation is complete. FIG. 18E demonstrates removal of the device 100 from the user, which allows the safety shield 104 to extend into an extended, post use position. FIG. 18F shows a force on the distal end of the safety shield 104 in its extended post-use position, to retract the safety shield 104, moving it toward the proximal end of the device while also retracting the plunger subassembly 126 proximally relative to the device 100. These steps may be used to reset the device to a pre-use position, in one embodiment, without the use of a reset cap. In another embodiment, these steps may be used to place the device in a safe-post use position by retracting the plunger assembly and the safety shield following use.

In some embodiments, the training device 100 may also include a vial to simulate a vial of a medicament containing drug delivery device. The vial may be associated with the plunger 112, such that it, too, would be retracted in this step, FIG. 18F. FIG. 18G shows insertion of a cap 160 onto the distal end of the device 100 following use of the device 100.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. A resettable injection training device, comprising:
 an outer housing comprising a proximal end and a distal end;
 an inner housing comprising a proximal end and a distal end;
 a safety shield moveable relative to the inner housing, the safety shield comprising a proximal end, a distal end, and having an extended pre-use position, an extended post-use position, and a retracted position;
 a lateral actuation member comprising a raised position and a depressed position;

a plunger having a proximal end and a distal end, the plunger moveable proximally and distally within the inner housing to simulate delivery of medicament;

a plunger subassembly comprising the plunger;

a first signal output signaling actuation of the device;

a second signal output signaling completion of an injection simulation; and a reset cap comprising a plunger interfacing portion and a safety shield interfacing portion for resetting the safety shield and the plunger;

wherein in a pre-use extended position, the safety shield is proximally moveable by applying a force to the distal end of the safety shield;

wherein in the raised position, the lateral actuation member is locked prior to movement of the safety shield from the extended, pre-use position to the retracted position;

wherein when the safety shield is moved from the extended, pre-use position to the retracted position, the lateral actuation member is unlocked for actuation; and wherein actuation of the lateral actuation member by movement from an unlocked position to a depressed position releases the plunger a to move distally relative to the housing, and locks the lateral actuation member in a depressed, locked position.

2. The resettable injection training device of claim 1, wherein distal plunger movement maintains the lateral actuation member in a depressed, locked position.

3. The resettable injection training device of claim 1, wherein release of the plunger causes the plunger subassembly to interface with a portion of the inner housing to deliver the first signal output.

4. The resettable injection training device of claim 1, further comprising a rotatable member associated with the plunger and a rotatable biasing member, the rotatable biasing member biasing the rotatable member in a first direction, and an interface between the plunger and the rotatable member maintaining the rotatable member in a second direction, wherein upon distal movement of the plunger simulating completion of medicament delivery, the rotatable biasing member rotates the rotatable member in the first direction until a portion of the rotatable member contacts the inner housing to deliver the second signal output, audibly signaling completion of the injection simulation.

5. The resettable injection training device of claim 1, wherein removal of the force on the distal end of the safety shield causes the safety shield to extend to an extended, post-use position.

6. The resettable injection training device of claim 5, wherein a force on the distal end of the safety shield causing proximal movement of the safety shield from the extended post-use position moves the plunger proximally.

7. The resettable injection training device of claim 6, wherein the safety shield further comprises a safety shield tab, and the plunger subassembly further comprises a ring member having a protrusion for interfacing with the safety shield tab, such that proximal movement of the safety shield from the extended post-use position causes the safety shield tab to interface with the ring member protrusion, also moving the plunger subassembly in a proximal direction with the safety shield.

8. The resettable injection training device of claim 1, wherein insertion of the reset cap into the distal end of the device and proximal movement of the cap relative to the device resets the safety shield from an extended post-use position to an extended, pre-use position upon removal of the reset cap from the device.

9. The resettable injection training device of claim 8, wherein reset of the plunger to a pre-use plunger position causes the plunger to interface with the rotatable member to reset the rotatable member and the rotatable biasing member to a pre-use position.

10. The resettable injection training device of claim 9, wherein the plunger comprises one or more plunger rails on its outer surface, said rails interface with one or more features on an inner portion of the rotatable member to cause the rotatable member to rotate in the second direction against the force of the rotatable biasing member to a pre-use position.

11. The resettable injection training device of claim 10, wherein further proximal movement of the reset cap into the distal end of the device causes disengagement of the actuation member depressed lock from the lateral actuation member, releasing the lateral actuation member to the raised, locked position and moving the actuation member depressed lock proximally.

12. The resettable injection training device of claim 11, wherein the device further comprises an actuation biasing member, biasing the lateral actuation member toward a raised position.

13. The resettable injection training device of claim 12, wherein further proximal movement of the reset cap into the distal end of the device biases the actuation member released lock spring and the actuation member depressed lock spring.

14. The resettable injection training device of claim 12, wherein upon release of the lateral actuation member to the raised, locked position, the actuation member released lock moves distally to a pre-use position.

15. The resettable injection training device of claim 1, wherein the first signal output is an audible signal.

16. The resettable injection training device of claim 1, wherein the second signal output is an audible signal.

17. A method of resetting the injection training device of claim 1, comprising:

inserting a reset cap comprising a safety shield interfacing portion, and a plunger interfacing portion into a distal end of the device, wherein the safety shield interfacing portion interfaces with the safety shield, such that insertion of the reset cap moves the safety shield proximally, and the plunger interfacing portion moves the plunger proximally, wherein the proximal movement of the reset cap causes the device to be reset from a pre-use position to a post-use position.

18. A method of resetting the injection training device of claim 1, comprising:

Depressing the safety shield from its extended post-use position, such that the safety shield is retracted into the device, and the plunger moves proximally to a retracted position.

19. A resettable injection training device, comprising:

an outer housing comprising a proximal end and a distal end;

an inner housing comprising a proximal end and a distal end;

a safety shield moveable relative to the inner housing, the safety shield comprising a proximal end, a distal end, and having an extended pre-use position, an extended post-use position, and a retracted position;

a lateral actuation member comprising a raised position and a depressed position;

a plunger having a proximal end and a distal end, the plunger moveable proximally and distally within the inner housing to simulate delivery of medicament;

a plunger subassembly comprising the plunger;

a first signal output signaling actuation of the device;

a second signal output signaling completion of an injection simulation; and a reset cap comprising a plunger interfacing portion and a safety shield interfacing portion for resetting the safety shield and the plunger; wherein insertion of the reset cap into the distal end of the device and proximal movement of the cap relative to the device resets the safety shield from an extended post-use position to an extended, pre-use position upon removal of the reset cap from the device.

20. A method of resetting the injection training device of claim 19, comprising:

Depressing the safety shield from its extended post-use position, such that the safety shield is retracted into the device, and the plunger moves proximally to a retracted position.

\* \* \* \* \*